US008929992B2

(12) United States Patent
Toader et al.

(10) Patent No.: US 8,929,992 B2
(45) Date of Patent: Jan. 6, 2015

(54) METHOD AND SYSTEM FOR DETERMINING SETTINGS FOR DEEP BRAIN STIMULATION

(75) Inventors: Emil Toader, Eindhoven (NL); Hubert Cécile François Martens, Eindhoven (NL); Michel Marcel Jose Decre, Eindhoven (NL); Franciscus Paulus Maria Budzelaar, Eindhoven (NL); Pieter Gerrit Blanken, Eindhoven (NL); David James Anderson, Ann Arbor, MI (US)

(73) Assignees: Sapiens Steering Brain Stimulation B.V. (NL); NeuroNexus Technologies Inc., Ann Arbor, MI (US)

( * ) Notice: Subject to any disclaimer, the term of this patent is extended or adjusted under 35 U.S.C. 154(b) by 17 days.

(21) Appl. No.: 13/581,484

(22) PCT Filed: Feb. 25, 2011

(86) PCT No.: PCT/IB2011/050809
§ 371 (c)(1),
(2), (4) Date: Oct. 9, 2012

(87) PCT Pub. No.: WO2011/107917
PCT Pub. Date: Sep. 9, 2011

(65) Prior Publication Data
US 2013/0030500 A1 Jan. 31, 2013

Related U.S. Application Data

(60) Provisional application No. 61/309,074, filed on Mar. 1, 2010.

(51) Int. Cl.
*A61N 1/36* (2006.01)
*A61N 1/05* (2006.01)
*A61N 1/00* (2006.01)

(52) U.S. Cl.
CPC ............... *A61N 1/0534* (2013.01); *A61N 1/00* (2013.01); *A61N 1/36185* (2013.01)
USPC .......................................................... 607/45

(58) Field of Classification Search
CPC ..... A61N 1/05; A61N 1/0551; A61N 1/0529; A61N 1/0534; A61N 1/0543; A61N 1/37241; A61N 1/36135; A61B 5/0478

USPC .............................. 607/2–9, 45–49, 115–119
See application file for complete search history.

(56) References Cited

U.S. PATENT DOCUMENTS

| 2004/0181263 | A1 | 9/2004 | Balzer et al. |
| 2007/0027514 | A1 | 2/2007 | Gerber |
| 2007/0129770 | A1* | 6/2007 | Younis ............................. 607/45 |
| 2008/0208268 | A1 | 8/2008 | Bartic et al. |

OTHER PUBLICATIONS

International Search Report and Written Opinion for International Patent Application No. PCT/IB2011/050809 dated Jun. 6, 2011.
First Office Action issued on Mar. 19, 2014 for Chinese Patent Application No. 201180011778.7.

* cited by examiner

*Primary Examiner* — Rex R Holmes
(74) *Attorney, Agent, or Firm* — Morgan, Lewis & Bockius LLP

(57) ABSTRACT

A method and a control system (20) are provided for determining a relation between stimulation settings for a brain stimulation probe (10) and a corresponding V-field. The brain stimulation probe (10) comprises multiple stimulation electrodes (11). The V-field is an electrical field in brain tissue surrounding the stimulation electrodes (11). The method comprises sequentially applying a test current to n stimulation electrodes (11), n being a number between 2 and the number of stimulation electrodes (11) of the brain stimulation probe (10), for each test current at one of the n stimulation electrodes (11), measuring a resulting excitation voltage at m stimulation electrodes, m being a number between 2 and the number of stimulation electrodes (11) of the brain stimulation probe (10), from the stimulation settings and the measured excitation voltages, deriving an (m*η) coupling matrix, an element (q, p) in the coupling matrix reflecting an amount of electrical impedance between two of the stimulation electrodes (11), and using the coupling matrix for determining the relation between the stimulation settings and the corresponding V-field.

10 Claims, 4 Drawing Sheets

METHOD AND SYSTEM FOR DETERMINING SETTINGS FOR DEEP BRAIN STIMULATION

CROSS-REFERENCE TO RELATED APPLICATIONS

This application is a U.S. National Stage of International Patent Application No. PCT/IB2011/050809 filed on Feb. 25, 2011, which claims priority to U.S. Provisional Patent Application No. 61/309,074 filed on Mar. 1, 2010, both of which are incorporated herein by reference in their entirety.

FIELD OF THE INVENTION

This invention relates to a method for determining a relation between stimulation settings for a brain stimulation probe and a corresponding V-field, the brain stimulation probe comprising multiple stimulation electrodes, the V-field being a potential distribution in brain tissue surrounding the stimulation electrodes.

This invention further relates to a computer program product and to a control system for determining such a relation.

BACKGROUND OF THE INVENTION

Deep brain stimulation (DBS) is a surgical treatment involving the implantation of a medical device, which sends electrical pulses to specific parts of the brain. A preferred DBS probe comprises a plurality of electrodes for providing stimulating electrical pulses at different positions in the target region. For example, the probe may comprise an array of 64 or 128 electrodes. DBS in selected brain regions has provided remarkable therapeutic benefits for otherwise treatment-resistant movement and affective disorders such as chronic pain, Parkinson's disease, tremor and dystonia. DBS surgery aims to electrically stimulate a target structure, while minimizing detrimental side-effects caused by stimulation of particular nearby neuronal structures. To make that possible, it is important to know the effect of particular stimulation settings on the electrical field that is generated in the brain tissue. Likewise, it is desirable to know what stimulation settings to apply in order to obtain an optimal stimulation volume.

In 'Electric field and stimulating influence generated by deep brain stimulation of the subthalamic nucleus' by McIntyre et al. (2004b), Clin Neurophys 115, 589-595, a method is disclosed for developing a quantitative understanding of the volume of axonal tissue directly activated by DBS of the subthalamic nucleus. The method uses finite element computer models (FEM) to address the effects of DBS in a medium with tissue conductivity properties derived from human diffusion tensor magnetic resonance data (MRI/DTI).

It is a disadvantage of the method of McIntyre et al. that an MRI/DTI system is needed for obtaining a conductivity map of the patient's brain. Additionally, DTI does not measure electrical conductivity directly but instead estimates one by assuming a theoretical relationship between water diffusion (measured by DTI) and electrical conductivity. Furthermore, the resolution of DTI for practical scanning times is limited to about 2 mm, i.e. 4 times the typical electrode pitch of high resolution DBS probes. It is also a problem that tissue conductivity changes over time, e.g. due to encapsulation of the probe, and that the known method requires a regular update of the conductivity map. Performing regular DTI scans is unpractical for that purpose.

OBJECT OF THE INVENTION

In view of the above, it is an object of the invention to provide a more practical or more accurate method for determining stimulation settings for a brain stimulation probe as described above.

SUMMARY OF THE INVENTION

According to a first aspect of the invention, this object is achieved by providing a method for determining a relation between stimulation settings for a brain stimulation probe and a corresponding V-field, the brain stimulation probe comprising multiple stimulation electrodes, the V-field being a potential distribution in brain tissue surrounding the stimulation electrodes, the method comprising: sequentially applying a test current to n stimulation electrodes, n being a number between 2 and the number of stimulation electrodes of the brain stimulation probe, for each test current at one of the n stimulation electrodes, measuring a resulting excitation voltage at m stimulation electrodes, m being a number between 2 and the number of stimulation electrodes of the brain stimulation probe, from the stimulation settings and the measured excitation voltages, deriving an (m*n) coupling matrix, an element $Z_{q,p}$ in the coupling matrix reflecting an amount of electrical impedance between two of the stimulation electrodes and using the coupling matrix for determining the relation between the stimulation settings and the corresponding V-field.

Electrical properties, typically impedances, of the brain tissue close to the electrodes are determined by applying the test currents and measuring excitation voltages. The coupling matrix comprises the determined electrical properties. An element $Z_{q,p}$ in the coupling matrix may, e.g., represent a ratio of the contribution to a voltage $V_q$ on electrode q and a test current $I_p$ injected in electrode p. These impedance values $Z_{q,p}$ depend on properties of the stimulation probe (e.g. electrode size, shape and material) and the surrounding system (e.g. brain tissue). It is to be noted that also the excitation voltage at the stimulated electrode itself may be measured. Such measurements will determine the diagonal elements in the (m*n) coupling matrix and reflect an impedance between the stimulated electrode and a ground electrode of the stimulation probe. The ground electrode or return electrode may be formed by the casing of the probe.

Alternatively, an impedance matrix Z may be generated by mathematical inversion of an admittance matrix. The elements of the admittance matrix can be determined by forcing a non-zero test voltage on a particular electrode while forcing zero voltage on all other electrodes. The elements of the admittance matrix are then obtained by measuring the currents in the electrodes necessary to create said voltages.

Using the information stored in the coupling matrix and some theoretical knowledge about electrical fields, the relation between stimulation settings and corresponding V-fields in the brain tissue are determined. Such a relation may, e.g., be provided in the form of a look-up table describing the expected V-field for unit current excitation of the single electrodes. Based on this relation and assuming a linear system (in a linear system, the superposition theorem, known from network theory, may be applied), it is then possible to calculate an expected V-field(I) for any possible combination of stimulation currents applied and, vice versa, to calculate the required combination of stimulation currents to obtain a target V-field.

Resulting V-fields in the brain tissue may, e.g., be determined using knowledge of the expected currents I=($I_1$, $I_2$, $I_3, \ldots, I_m$) or potentials $V=(V_1, V_2, V_3, \ldots, V_m)$ at each electrode of the stimulation probe. In a similar way, it may be calculated what currents I or electrode potentials V are needed for obtaining target V-field in the brain tissue. A relation between the electrode potentials V or currents I and the stimulation settings is derivable from the coupling matrix.

The main advantage of the method according to the invention is that it does not require imaging devices for deriving electrical properties from anatomical images. According to the invention, the electrical properties of the brain tissue are derived from the impedance measurements and no electrical properties have to be determined indirectly, by analyzing anatomical images. The fact that no imaging apparatus is needed for determining the relation between the stimulation settings and the corresponding V-field makes it much easier to update the relation over time. Updating the relation may, e.g., be needed because tissue conductivity may change due to encapsulation of the probe. Furthermore, the method according to the invention may be used to provide more accurate estimations of required stimulation settings and/or expected V-fields. The resolution of known imaging techniques like DTI is about 4 times the typical electrode pitch of the stimulation probe, while the method according to the invention provides detailed information on the electrical properties of brain tissue close to each separate stimulation electrode.

According to a second aspect of the invention, a control system is provided, comprising means for applying test currents to the stimulation electrodes, means for measuring excitation voltages at the stimulation electrodes and a processor arranged for performing the method according to the invention.

These and other aspects of the invention are apparent from and will be elucidated with reference to the embodiments described hereinafter.

DETAILED DESCRIPTION OF THE INVENTION

Figure 1:
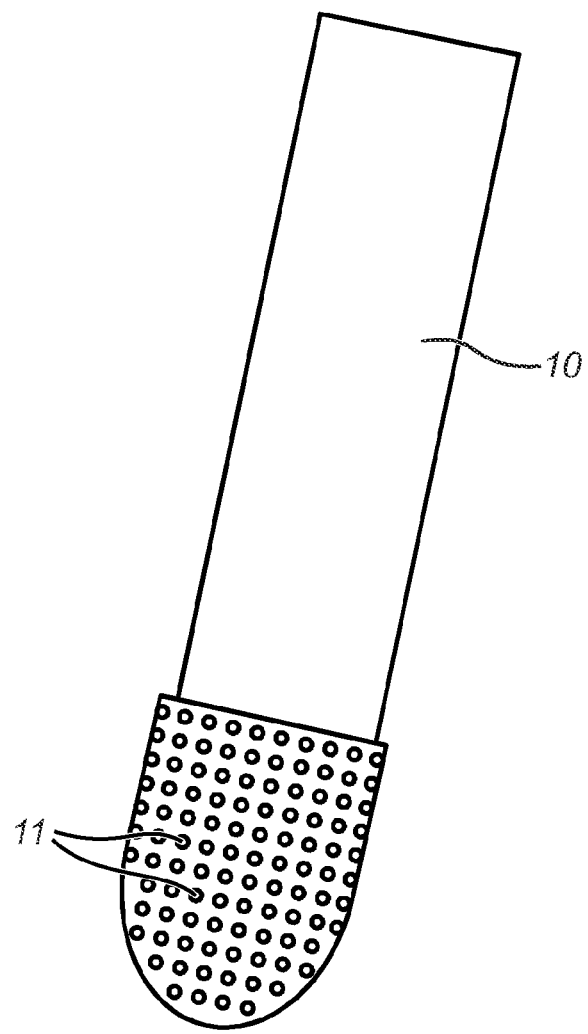
FIG. 1 schematically shows a stimulation probe with a plurality of stimulation electrodes.

FIG. 1 schematically shows a brain stimulation probe 10 with a plurality of stimulation electrodes 11. It is to be noted that this is just a schematic drawing and the actual stimulation probe 10 used may be quite different. What is important for the stimulation probe 10 used in the method and system according to the invention is that it has a plurality of stimulation electrodes 11 distributed over at least part of the probe surface. For example, an array of 64 or 128 electrodes is used.

Figure 2:
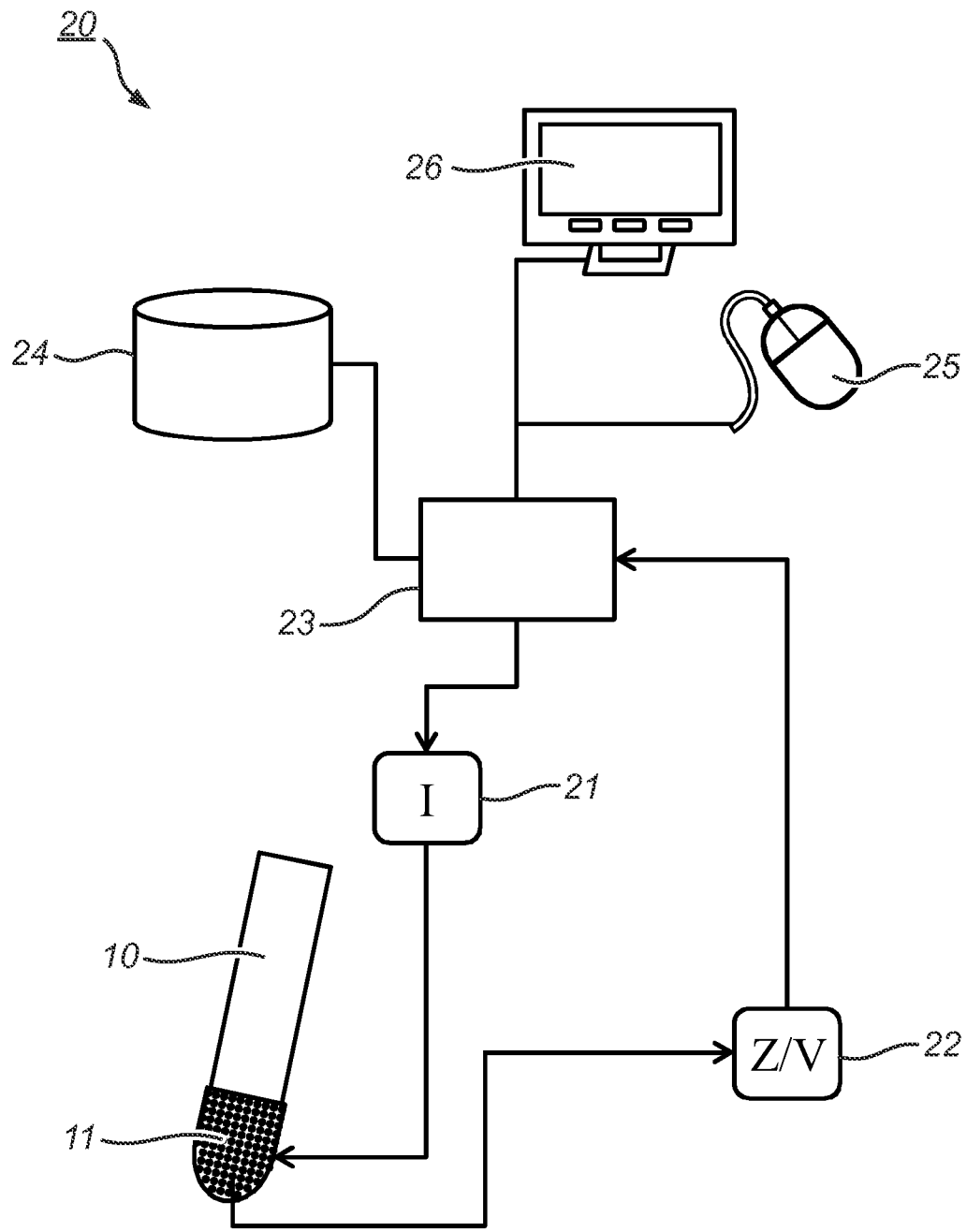
FIG. 2 shows a block diagram of a control system according to the invention.

FIG. 2 schematically shows a control system 20 for controlling the brain stimulation probe 10 of FIG. 1. The stimulation probe 10 is coupled to a processor 23 via a pulse generator 21. The processor 23 determines and controls the stimulation settings to be applied to the stimulation electrodes 11 for enabling proper functioning of the stimulation probe 10. The pulse generator 21 provides the electrical signals, e.g. currents, to the individual stimulation electrodes 11, in accordance with instructions from the processor 23. The processor 23 is also capable of receiving data and signals from the stimulation electrodes 11 in order to obtain information about the functioning of the stimulation probe 10 and its interaction with the environment. An impedance recording means or voltmeter 22 is provided for measuring excitation voltages at the electrodes 11 adjacent to or further away from an electrode 11 receiving an electrical current. The processor 23 is further coupled to a memory 24 for storing, e.g., patient data and software for controlling the system 20 and the method according to the invention. The control system 20 may be coupled to a local or wide area network (e.g. the Internet) for being able to exchange or share data with other systems.

In an embodiment, the number of independent current sources (e.g. 4) to generate stimulation is less than the number of electrodes (e.g. 64). The output of a single current source may be distributed to several electrodes simultaneously. The current of the common source is distributed over the electrodes in dependence of individual electrodes tissue impedance and lead-impedance to the individual sites. Stimulation settings may be defined as current generator current values combined with connection settings, i.e. to which electrodes the pulse generators are connected. Knowing the stimulation settings of electrodes to the current sources and using the coupling matrix the stimulation currents I (on all electrodes) may be calculated.

Additionally, a display 26 may be coupled to the processor 23 for showing information that may help a user with configuring or using the system 20. The system 20 may additionally comprise user input means, such as a mouse 25 or other type of pointer device and/or a keyboard. The display 26 may also be used for providing a graphical user interface for enabling a user to configure and control the system 20. For that purpose, the display 26 might also have touch screen functionality.

Figure 3:
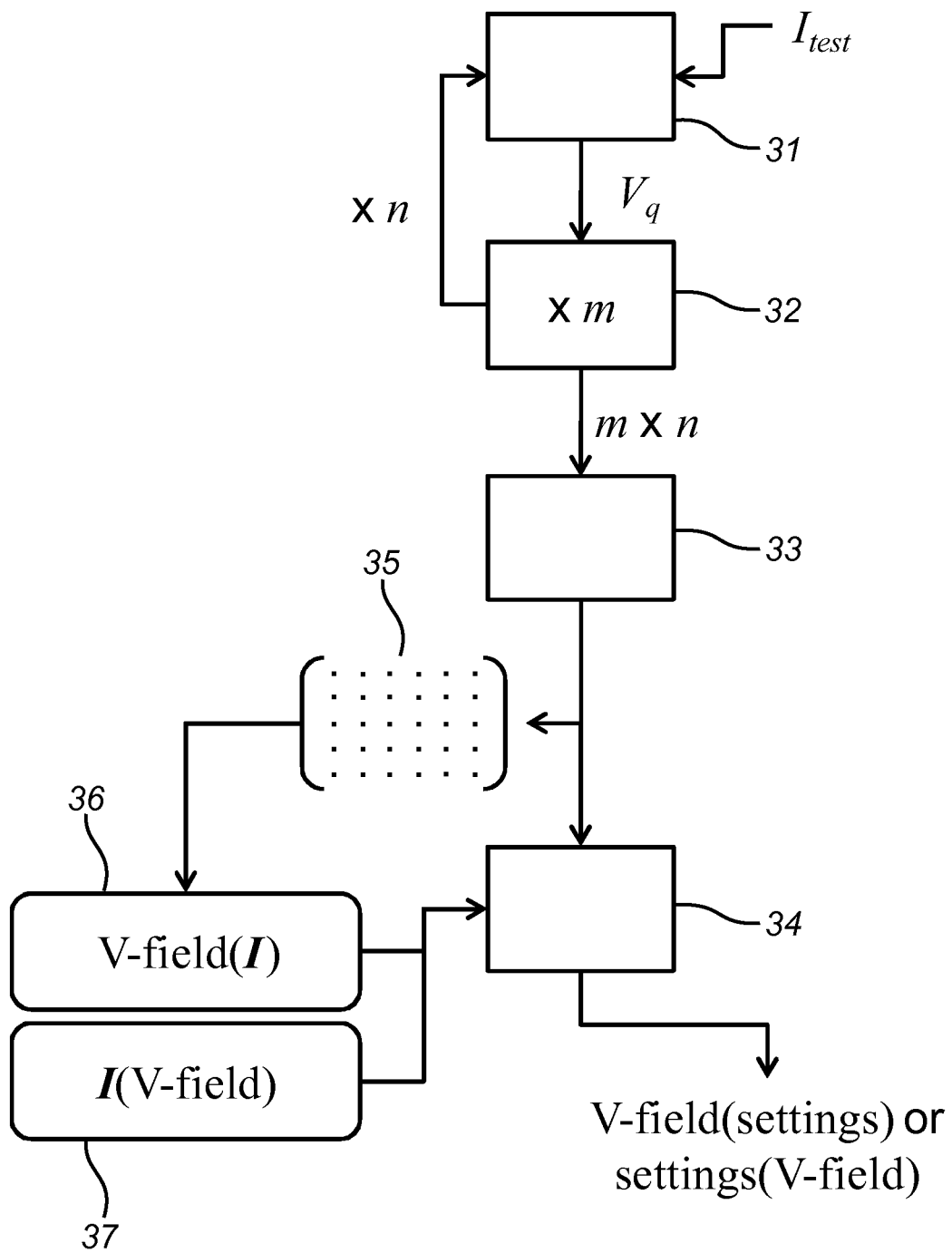
FIG. 3 shows a flow diagram of a method for determining a relation between stimulation settings for a brain stimulation probe and a corresponding V-field.

FIG. 3 shows a flow diagram of a method for determining a relation between stimulation settings for a brain stimulation probe 10 and a corresponding V-field. The method starts with an excitation step 31 in which the pulse generator 21 is used for sequentially exciting each stimulation electrode 11 or a sub-group of selected stimulation electrodes 11 with a known test current, $I_{test}$. When a test pulse is applied to one of the stimulation electrodes 11, the impedance recording means or voltmeter 22 measures an excitation voltage at said electrode 11 and response voltages at other stimulation electrodes 11 in response recording step 32. The response may be recorded as electrode voltage $V_{q,p}$ at the stimulation electrode q due to excitation at electrode p or as measured impedance value $Z_{q,p}$. This measurement may be performed for all stimulation electrodes 11 or for a number m of selected, e.g. neighboring, stimulation electrodes 11. After exciting a first stimulation electrode 11 and measuring the responses on the m electrodes 11, a subsequent stimulation electrode 11 may be tested. When n electrodes are excited and voltages are recorded on m electrodes, the first two steps 31, 32 are performed at least n times. Optionally, some or all stimulation electrodes 11 are tested twice or more, possibly with different test currents, $I_{test}$. The result of response recording step 32, is m*n measurements of combined electrical properties of the probe 10 and the tissue surrounding the probe 10. In matrix generating step 33, this information may be processed to form an m*n coupling matrix 35.

In practice, the number of tested electrodes, n, will often equal the number of recording electrodes, m. This coupling matrix 35 captures the effects of the inhomogeneous anisotropic tissue conductivity, i.e. its elements reflect the amount of electrical tissue impedance between various sites. For example, an entry (q, p) in the coupling matrix 35 may hold the ratio of the voltage on electrode q and the current injected into electrode p. In a preferred embodiment, also the excitation voltage at the stimulated electrode itself is be measured. Such measurements will determine the diagonal elements in the (m*n) coupling matrix and reflect an impedance between the stimulated electrode and a ground electrode of the stimulation probe. The ground electrode or return electrode may be formed by the casing of the probe.

With the coupling matrix 35 it is possible to determine a pattern of expected electrode voltages V at each of the electrodes 11 in response to a particular pattern of stimulation currents I. Similarly, it is possible to determine the required pattern of stimulation currents I needed to obtain a desired pattern of electrode voltages V.

For proper operation of the probe 10 it may not yet be enough to know what electrode potentials V are caused by what stimulation currents I and vice versa. In step 34 of FIG. 3, the coupling matrix 35 is used to calculate an expected potential distribution (V-field) in the brain tissue for a given pattern of stimulation currents or to calculate a required stimulation pattern to obtain a desired V-field. Calculating the V-field from individual electrode potentials V or currents I may, e.g., be done using finite element modeling (FEM) or other numerical techniques. The V-field may be calculated under the assumption of homogeneous tissue conductivity, but is preferably corrected by measured data available from the coupling matrix 35. The relation 36, 37 between individual electrode potentials V or currents I and the V-field also depends on the composition of the brain tissue. The coupling matrix 35 comprises information about this composition and may thus be used to provide a more accurate determination of the relation between V-field and electrode potentials V or currents I.

Figure 4:
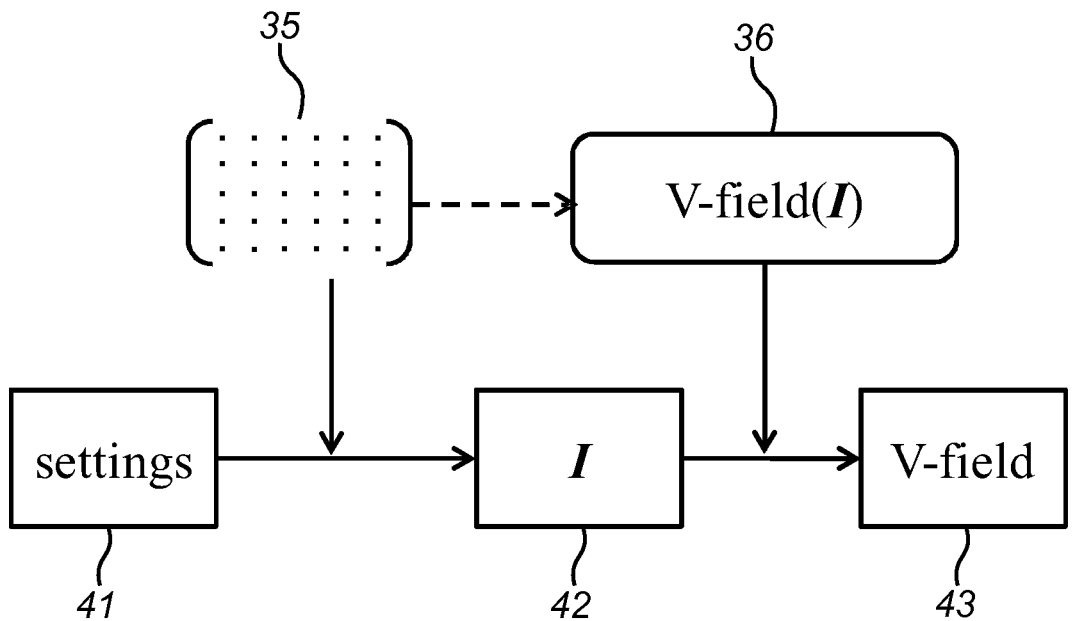
FIG. 4 shows a flow diagram of a method of determining an expected V-field.
Figure 5:
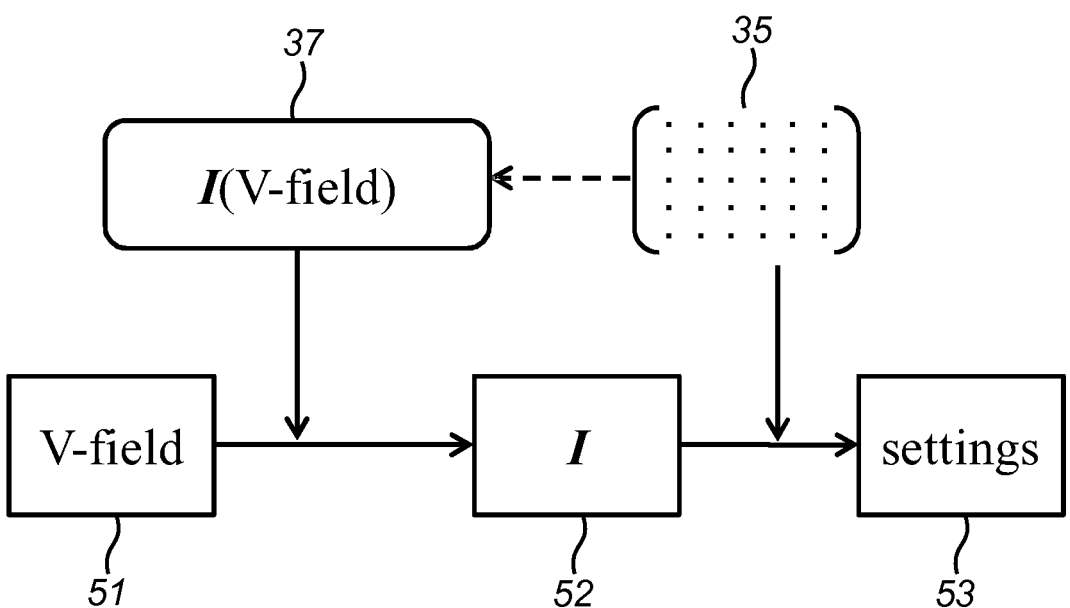
FIG. 5 shows a flow diagram of a method of determining required stimulation settings for obtaining a target V-field.

FIGS. 4 and 5 show exemplary flow diagrams of methods for realizing step 34 in FIG. 3. In these methods the coupling matrix 35 and the knowledge about the relation between individual electrode currents I and the V-field are used to determine required stimulation settings or expected V-fields. FIG. 4 shows a method of determining an expected V-field and FIG. 5 shows a method of determining required stimulation settings for obtaining a target V-field.

In FIG. 4 it is shown how an expected V-field is calculated for a particular set of stimulation settings. First the stimulation settings are provided (step 41), e.g. in the form of pulse generator currents and connections settings for the electrically coupling of the n electrodes 11 to the pulse generators. Then, the coupling matrix 35 is used for determining (step 42) the resulting currents $I_1, I_2, \ldots, I_q, \ldots, I_m$, at the electrodes 11. When the electrode currents $I_1, I_2, \ldots, I_q, \ldots, I_m$ at the electrodes 11 are known, the relation 36 between electrode currents I=$I_1, I_2, \ldots, I_q, \ldots, I_m$ and V-field is used for calculating (step 43) the resulting V-field. It is to be noted that the coupling matrix 35 is obtained using measurements as described above with reference to FIG. 3. The coupling matrix for an implanted probe 10 has at least to be determined once. However, the coupling matrix 35 is preferably updated periodically in order to take into account the changes, e.g., in the brain tissue that may occur over time. The relation 36 between electrode currents I and V-field may be computed once under the assumption of homogeneous tissue conductivity, but is preferably corrected by measured data available from the coupling matrix 35. The relation 36 may be updated together with the coupling matrix 35.

In FIG. 5 it is shown how the stimulation settings are determined which are needed for obtaining a target V-field. First a description of the target V-field is provided (step 51), e.g. in the form of a set of coordinates of positions target structures in the brain, which target structures are to be stimulated. Alternatively (or additionally), coordinates are provided describing positions of neuronal structures for which stimulation should be avoided. Then the relation 37 between the V-field and individual electrode currents I is used to calculate (step 52) the electrode currents I needed to obtain the desired V-field. Using the coupling matrix 35, the stimulation settings for obtaining these required electrode currents I are then determined (step 53).

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim.

The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A method for determining a relation between stimulation settings for a brain stimulation probe and a corresponding V-field, the brain stimulation probe comprising multiple stimulation electrodes, the V-field being a potential distribution in brain tissue surrounding the stimulation electrodes, the method comprising:

sequentially applying a test current to n stimulation electrodes, n being a number between 2 and the number of stimulation electrodes of the brain stimulation probe;

for each test current at one of the n stimulation electrodes, measuring a resulting excitation voltage at m stimulation electrodes, m being a number between 2 and the number of stimulation electrodes of the brain stimulation probe;

from the stimulation settings and the measured excitation voltages, deriving an (m*n) coupling matrix having m lines and n columns, an entry $Z_{q,p}$ in the coupling matrix reflecting an amount of electrical impedance between two of the stimulation electrodes and positioned on line q and column p of the coupling matrix, where q is an integer number between 1 and m, and p is an integer number between 1 and n, $Z_{q,p}$ being related to a voltage obtained on an electrode q when a current is applied on electrode p, and where the electrode q and the electrode p are selected from the n stimulation electrodes; and using the coupling matrix for determining the relation between the stimulation settings and the corresponding V-field.

2. The method for determining the relation between stimulation settings for the brain stimulation probe and the corresponding V-field as claimed in claim 1, the method further comprising:

receiving a predetermined set of stimulation settings; and using the relation between the stimulation settings and the corresponding V-field for determining the V-field corresponding to the predetermined set of stimulation settings.

3. The method for determining the relation between stimulation settings for the brain stimulation probe and the corresponding V-field as claimed in claim 1, the method further comprising:

receiving a description of a target V-field; and using the relation between the stimulation settings and the corresponding V-field for determining a set of required stimulation settings for obtaining the target V-field.

4. A computer program product for determining the relation between stimulation settings for the brain stimulation probe and the corresponding V-field, which program is operative to cause a processor to perform the method as claimed in claim 1.

5. A control system for determining a relation between stimulation settings for a brain stimulation probe and a corresponding V-field, the brain stimulation probe comprising multiple stimulation electrodes, the V-field being a potential distribution in brain tissue surrounding the stimulation electrodes, the control system comprising:

means for applying test currents to the stimulation electrodes;

means for measuring an excitation voltage resulting from the applied test currents; and a processor being arranged for instructing the means for applying test currents to sequentially apply a test current to n stimulation electrodes, n being a number between 2 and the number of stimulation electrodes of the brain stimulation probe;

instructing the means for measuring the excitation voltage to measure at m stimulation electrodes an excitation voltage caused by each test current, m being a number between 2 and the number of stimulation electrodes of the brain stimulation probe;

from the stimulation settings and the measured excitation voltages, deriving an (m*n) coupling matrix having m lines and n columns, an entry $Z_{q,p}$ in the coupling matrix reflecting an amount of electrical impedance between two of the stimulation electrodes and positioned on line q and column p of the coupling matrix, where q is an integer number between 1 and m, and p is an integer number between 1 and n, $Z_{q,p}$ being related to a voltage obtained on an electrode q when a current is applied on electrode p, and where the electrode q and the electrode p are selected from the n stimulation electrodes; and using the coupling matrix for determining the relation between the stimulation settings and the corresponding V-field.

6. A method for determining a relation between stimulation settings for a brain stimulation probe and a corresponding V-field, the brain stimulation probe comprising multiple stimulation electrodes, the V-field being a potential distribution in brain tissue surrounding the stimulation electrodes, the method comprising:

sequentially applying a test current to n stimulation electrodes, n being a number between 2 and the number of stimulation electrodes of the brain stimulation probe;

for each test current at one of the n stimulation electrodes, measuring a resulting excitation voltage at m stimulation electrodes, m being a number between 2 and the number of stimulation electrodes of the brain stimulation probe;

from the stimulation settings and the measured excitation voltages, deriving an (m*n) coupling matrix having m lines and n columns, an entry $Z_{q,p}$ in the coupling matrix reflecting an amount of electrical impedance between two of the stimulation electrodes and positioned on line q and column p of the coupling matrix, where q is an integer number between 1 and m, and p is an integer number between 1 and n, $Z_{q,p}$ being related to a voltage obtained on an electrode q when a current is applied on electrode p, and where the electrode q and the electrode p are selected from the n stimulation electrodes;

using the coupling matrix for determining the relation between the stimulation settings and the corresponding V-field;

forcing a non-zero test voltage on a particular electrode of the stimulation electrodes while forcing zero voltage on all other electrodes;

measuring the resulting currents in the electrodes necessary to create said forced voltages;

determining an admittance matrix, the elements of the admittance matrix reflecting the measured resulting currents; and generating the coupling matrix by mathematical inversion of the admittance matrix.

7. The method for determining the relation between stimulation settings for the brain stimulation probe and the corresponding V-field as claimed in claim 6, the method further comprising:
  receiving a predetermined set of stimulation settings; and
  using the relation between the stimulation settings and the corresponding V-field for determining the V-field corresponding to the predetermined set of stimulation settings.

8. The method for determining the relation between stimulation settings for the brain stimulation probe and the corresponding V-field as claimed in claim 6, the method further comprising:
  receiving a description of a target V-field; and
  using the relation between the stimulation settings and the corresponding V-field for determining a set of required stimulation settings for obtaining the target V-field.

9. A computer program product for determining the relation between stimulation settings for the brain stimulation probe and the corresponding V-field, which program is operative to cause a processor to perform the method as claimed in claim 6.

10. A control system for determining a relation between stimulation settings for a brain stimulation probe and a corresponding V-field, the brain stimulation probe comprising multiple stimulation electrodes, the V-field being a potential distribution in brain tissue surrounding the stimulation electrodes, the control system comprising:
  means for applying test currents to the stimulation electrodes;
  means for measuring an excitation voltage resulting from the applied test currents; and
  a processor being arranged for
    instructing the means for applying test currents to sequentially apply a test current to n stimulation electrodes, n being a number between 2 and the number of stimulation electrodes of the brain stimulation probe;
    instructing the means for measuring the excitation voltage to measure at m stimulation electrodes an excitation voltage caused by each test current, m being a number between 2 and the number of stimulation electrodes of the brain stimulation probe;
    from the stimulation settings and the measured excitation voltages, deriving an (m*n) coupling matrix having m lines and n columns, an entry $Z_{q,p}$ in the coupling matrix reflecting an amount of electrical impedance between two of the stimulation electrodes and positioned on line q and column p of the coupling matrix, where q is an integer number between 1 and m, and p is an integer number between 1 and n, $Z_{q,p}$ being related to a voltage obtained on an electrode q when a current is applied on electrode p, and where the electrode q and the electrode p are selected from the n stimulation electrodes;
    using the coupling matrix for determining the relation between the stimulation settings and the corresponding V-field;
    instructing the means for applying test currents to force a non-zero test voltage on a particular electrode of the multiple stimulation electrodes while forcing zero voltage on all other electrodes;
    instructing the means for measuring the excitation voltage to measure the resulting currents in the electrodes necessary to create said forced voltages;
    determining an admittance matrix, the elements of the admittance matrix reflecting the measured resulting currents; and
    generating the coupling matrix by mathematical inversion of the admittance matrix.

* * * * *